United States Patent
Kim et al.

(10) Patent No.: US 11,794,167 B2
(45) Date of Patent: Oct. 24, 2023

(54) METHOD FOR PRODUCING LACTIC ACID FROM WASTE PAPER USING LANTHANIDE-BASED METAL CATALYST

(71) Applicant: KOREA INSTITUTE OF SCIENCE AND TECHNOLOGY, Seoul (KR)

(72) Inventors: Kwang Ho Kim, Seoul (KR); Chang Soo Kim, Seoul (KR); Jeong-Myeong Ha, Seoul (KR); Jae Wook Choi, Seoul (KR); Chunjae Yoo, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/741,885

(22) Filed: May 11, 2022

(65) Prior Publication Data
US 2022/0379286 A1    Dec. 1, 2022

(30) Foreign Application Priority Data
Jun. 1, 2021    (KR) .......................... 10-2021-0071043

(51) Int. Cl.
*B01J 23/10*    (2006.01)
*C07C 51/487*    (2006.01)

(52) U.S. Cl.
CPC ............. *B01J 23/10* (2013.01); *C07C 51/487* (2013.01)

(58) Field of Classification Search
CPC .............................. B01J 23/10; C07C 51/487
USPC ................................................ 502/302–304
See application file for complete search history.

(56) References Cited

U.S. PATENT DOCUMENTS

| | | | |
|---|---|---|---|
| 9,260,359 B2 * | 2/2016 | Masuno | ................... C07C 15/08 |
| 9,708,760 B2 * | 7/2017 | Luo | .......................... D21H 17/07 |
| 2004/0147714 A1 | 7/2004 | Watanabe et al. | |

FOREIGN PATENT DOCUMENTS

| | | |
|---|---|---|
| KR | 10-2003-0030575 A | 4/2003 |
| KR | 10-2004-0022283 A | 3/2004 |
| KR | 10-2004-0027505 A | 4/2004 |
| KR | 10-2013-0116146 A | 10/2013 |
| KR | 10-2015-0029777 A | 3/2015 |
| KR | 10-1686337 B1 | 12/2016 |
| KR | 10-2088764 B1 | 3/2020 |

OTHER PUBLICATIONS

Liu, Dajiang, et al. "Cascade Production of Lactic Acid from Universal Types of Sugars Catalyzed by Lanthanum Triflate." ChemSusChem 11.3 (2018): 598-604.
Korean Office Action dated Apr. 14, 2023, in counterpart Korean Patent Application No. 10-2021-0071043 (4 pages in English, 4 pages in Korean).

* cited by examiner

*Primary Examiner* — Cam N. Nguyen
(74) *Attorney, Agent, or Firm* — NSIP Law

(57) ABSTRACT

Disclosed are a method for producing lactic acid from wastes containing cellulose and/or hemicellulose and a catalyst for thermochemical conversion reaction of wastes containing cellulose and/or hemicellulose. The method includes a step of adding a metal catalyst to wastes containing cellulose and/or hemicellulose and performing thermochemical conversion reaction. The method provides an effect of producing lactic acid from discarded wastes, e.g., waste paper such as waste corrugated paperboards, waste paper boxes, waste newspapers, etc.

6 Claims, 3 Drawing Sheets

[FIG. 1]
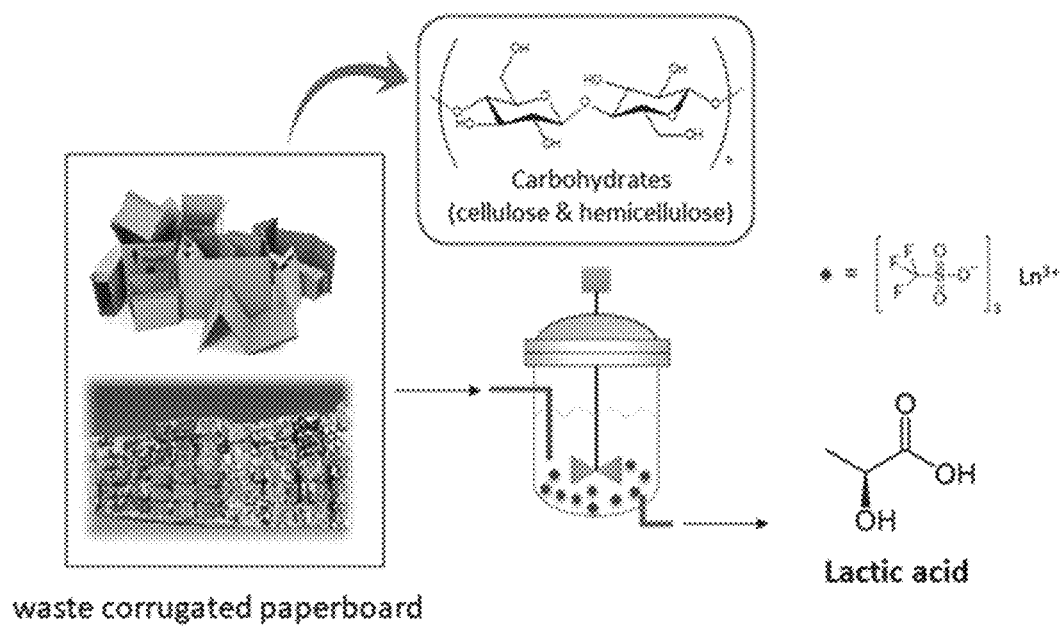
[FIG. 2]
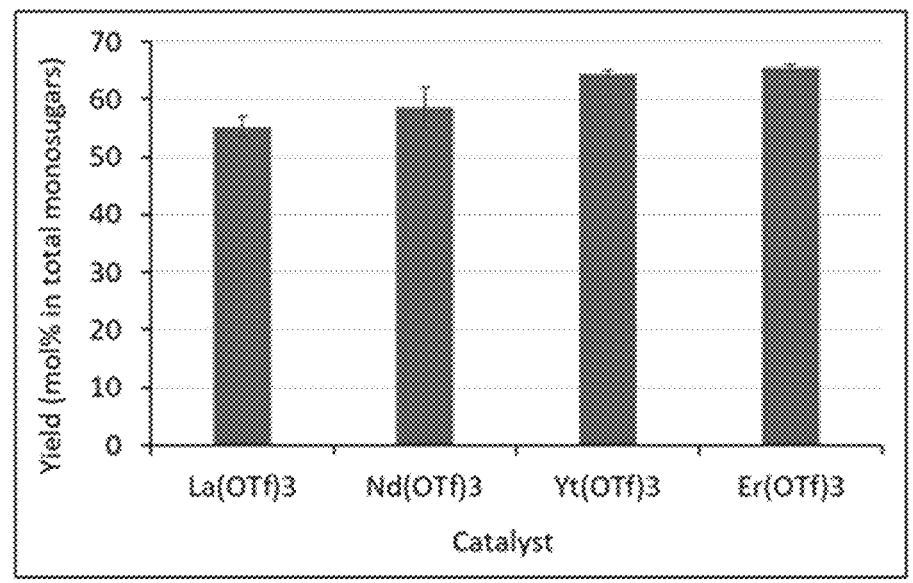

[FIG. 3]
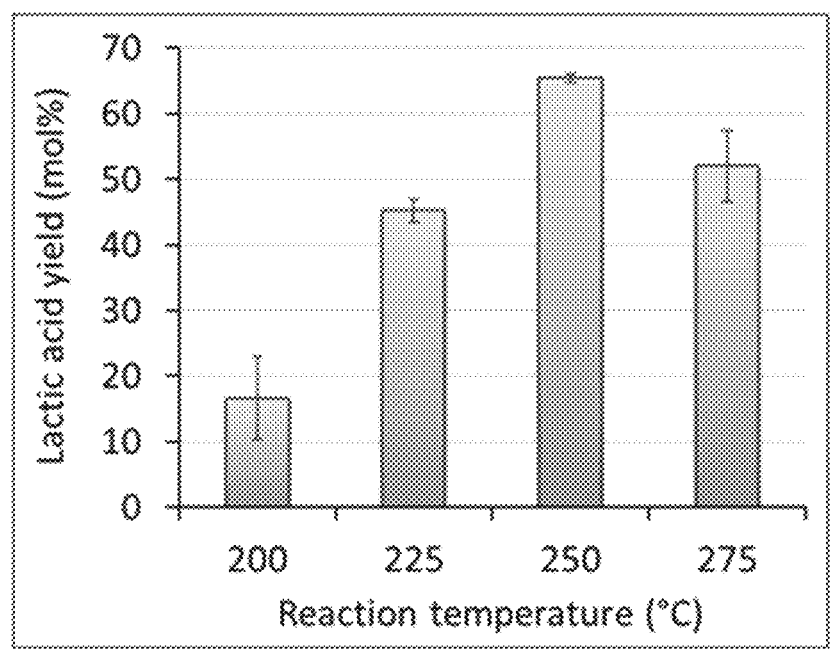
[FIG. 4]
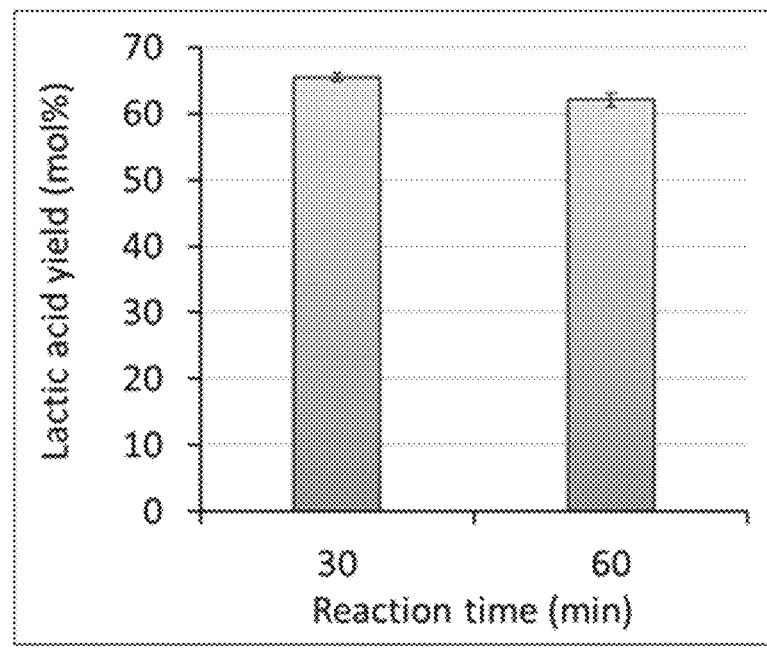

[FIG. 5]
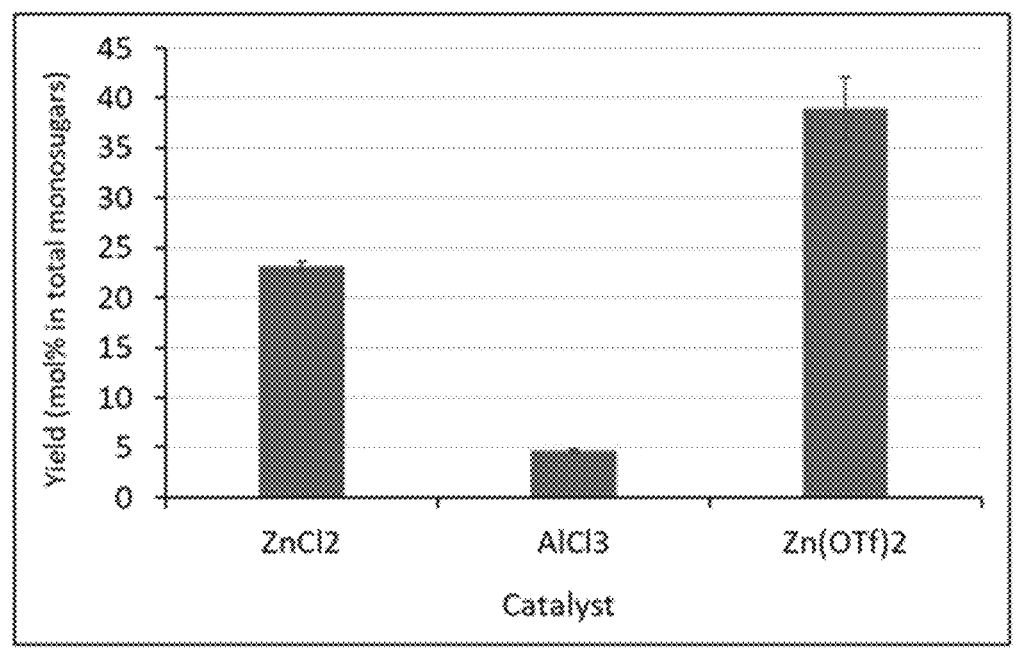

METHOD FOR PRODUCING LACTIC ACID FROM WASTE PAPER USING LANTHANIDE-BASED METAL CATALYST

CROSS-REFERENCES TO RELATED APPLICATIONS

This application claims the benefit under 35 U.S.C. 119(a) priority of Korean Patent Application No. 10-2021-0071043, filed with the Korean Intellectual Property Office on Jun. 1, 2021, the disclosure of which is incorporated herein by reference in its entirety.

BACKGROUND OF THE INVENTION

1. Field of the Invention

The present disclosure discloses a method for producing lactic acid from wastes containing cellulose and/or hemicellulose and a catalyst for thermochemical conversion reaction of wastes containing cellulose and/or hemicellulose.

2. Description of the Related Art

Reckless use of plastic materials derived from fossil resources and wastes occurring therefrom are the biggest social/environmental problems faced by the mankind. Therefore, many efforts are being made to develop biodegradable plastics and, through this, replace the existing plastics produced from fossil resources.

Polylactic acid (PLA) is one of the most representative biodegradable plastics and accounts for the largest demand and supply in the biodegradable bioplastics market at present. PLA is a polyester-based polymer material polymerized from lactide, which is a dimer of lactic acid, and can be utilized in various applications such as films, sheets, fibers, etc.

Lactic acid, the raw material of PLA, is produced industrially by petrochemical synthesis processes and biotechnological fermentation processes. Recently, owing to the social and environmental issues of the petrochemical processes, production of lactic acid through biotechnological fermentation processes using renewable biomass as raw materials is drawing attentions.

However, the biotechnological production of lactic acid through a microbial fermentation process requires a saccharification process of converting carbohydrates existing in biomass to monosaccharides and a fermentation process. Therefore, it is less efficient than common thermochemical conversion processes in terms of time and cost. In addition, the constituent materials such as lignin, etc. present in the biomass material decrease the yield of final products including lactic acid by inhibiting the saccharification and fermentation processes.

Meanwhile, with the recent active on-line commerce via the Internet, waste paper boxes are increasing appreciably owing to rapidly increased delivery services. These wastes are generally incinerated and it costs a lot. Therefore, efforts are being made to utilize the waste resources such as waste corrugated paperboards, waste paper, etc. as biomass resources.

At present, lactic acid is produced mostly from sugar/starch-based edible resources. However, in the future, use of the resources as raw materials for chemical products will incur social cost due to population growth and increased demand. Accordingly, it is desired to replace the sugar/starch-based edible resources as the raw materials for lactic acid production with biomass. In addition, in consideration of price competitiveness and sustainability, it is urgently required to develop a process for producing lactic acid from currently unused waste resources.

BRIEF SUMMARY OF THE INVENTION

The present disclosure provides a method for producing lactic acid from wastes by a thermochemical process using wastes containing cellulose and/or hemicellulose, e.g., waste paper, as a substrate and using a metal catalyst.

In an aspect, the present disclosure provides a method for producing lactic acid from wastes, which includes a step of adding a metal catalyst to wastes containing cellulose and/or hemicellulose.

In an exemplary embodiment, the wastes may be waste paper.

In an exemplary embodiment, the metal catalyst may include a lanthanide metal catalyst.

In an exemplary embodiment, the metal catalyst may include a lanthanide triflate metal catalyst.

In an exemplary embodiment, the lanthanide triflate metal catalyst may be one or more selected from a group consisting of lanthanum triflate, cerium triflate, praseodymium triflate, neodymium triflate, promethium triflate, samarium triflate, europium triflate, gadolinium triflate, terbium triflate, dysprosium triflate, holmium triflate, erbium triflate, thulium triflate, ytterbium triflate and lutetium triflate.

In an exemplary embodiment, the metal catalyst may be in an amount of 0.25-0.5 mmol per 1 g of the wastes.

In an exemplary embodiment, the metal catalyst may be added after the wastes are mixed with a solvent.

In an exemplary embodiment, the method may further include a step of performing thermochemical conversion reaction after adding the metal catalyst.

In an exemplary embodiment, the thermochemical conversion reaction may be performed at 200-300° C.

In an exemplary embodiment, the thermochemical conversion reaction may be performed for 20-70 minutes.

In another aspect, the present disclosure provides lactic acid produced by the method.

In another aspect, the present disclosure provides a catalyst for thermochemical conversion reaction of wastes containing cellulose and/or hemicellulose, which includes a lanthanide metal.

In an exemplary embodiment, the wastes may be waste paper.

In an exemplary embodiment, the lanthanide metal may include a lanthanide triflate metal.

In an exemplary embodiment, the lanthanide triflate may be one or more selected from a group consisting of lanthanum triflate, cerium triflate, praseodymium triflate, neodymium triflate, promethium triflate, samarium triflate, europium triflate, gadolinium triflate, terbium triflate, dysprosium triflate, holmium triflate, erbium triflate, thulium triflate, ytterbium triflate and lutetium triflate.

In an exemplary embodiment, the catalyst may be mixed in an amount of 0.25-0.5 mmol per 1 g of the wastes.

In an exemplary embodiment, the catalyst may be mixed with a mixture of the wastes and a solvent.

In an exemplary embodiment, lactic acid may be produced from the wastes containing cellulose and/or hemicellulose by the thermochemical conversion reaction.

In an exemplary embodiment, the thermochemical conversion reaction may be performed at 200-300° C.

In an exemplary embodiment, the thermochemical conversion reaction may be performed for 20-70 minutes.

In an aspect, the present disclosure provides a method for producing lactic acid using discarded wastes, e.g., waste paper such as waste corrugated paperboards, waste paper boxes, waste newspapers, etc. as a raw material.

In another aspect, the present disclosure provides a thermochemical conversion process for effectively producing lactic acid from waste resources in short time.

In another aspect, the present disclosure provides lactic acid produced by the method.

In another aspect, the present disclosure provides a catalyst for thermochemical conversion reaction of wastes containing cellulose and/or hemicellulose, which is used for producing lactic acid from wastes containing cellulose and/or hemicellulose.

BRIEF DESCRIPTION OF THE SEVERAL VIEWS OF THE DRAWING(S)

FIG. 1 schematically shows a process for producing lactic acid according to an exemplary embodiment of the present disclosure.

FIG. 2 shows lactic acid production yield depending on metal catalysts according to an exemplary embodiment of the present disclosure.

FIG. 3 shows lactic acid production yield depending on thermochemical conversion reaction temperature according to an exemplary embodiment of the present disclosure.

FIG. 4 shows lactic acid production yield depending on thermochemical conversion reaction time according to an exemplary embodiment of the present disclosure.

FIG. 5 shows lactic acid production yield depending on metal catalysts according to a comparative example.

DETAILED DESCRIPTION OF THE INVENTION

Hereinafter, the present disclosure is described in detail.

In an aspect, the present disclosure provides a method for producing lactic acid from wastes, which includes a step of adding a metal catalyst to wastes containing cellulose and/or hemicellulose.

In an exemplary embodiment, both L- and D-lactic acid may be produced by the method.

In an exemplary embodiment, the wastes may be waste paper and/or wood.

In an exemplary embodiment, the waste paper may be waste paper boxes, waste corrugated paperboards, waste newspapers, etc.

In an exemplary embodiment, the metal catalyst may include a lanthanide metal catalyst.

In an aspect, lactic acid can be produced from the carbohydrate components in the wastes in short time with high yield by using a lanthanide metal catalyst.

In an exemplary embodiment, the metal catalyst may include a lanthanide triflate metal catalyst.

In an exemplary embodiment, the lanthanide triflate metal catalyst may be one or more selected from a group consisting of lanthanum triflate, cerium triflate, praseodymium triflate, neodymium triflate, promethium triflate, samarium triflate, europium triflate, gadolinium triflate, terbium triflate, dysprosium triflate, holmium triflate, erbium triflate, thulium triflate, ytterbium triflate and lutetium triflate.

In an exemplary embodiment, the metal catalyst may be added in an amount of 0.25-0.5 mmol per 1 g of the wastes.

In an exemplary embodiment, the metal catalyst may be added after the wastes are mixed with a solvent.

In an exemplary embodiment, the solvent may include water.

In an exemplary embodiment, the thermochemical conversion reaction may be performed after the metal catalyst is added.

In an exemplary embodiment, the thermochemical conversion reaction may be performed under an inert atmosphere by supplying an inert gas.

In an exemplary embodiment, the inert gas may be nitrogen or helium.

In an exemplary embodiment, the inert gas may be supplied at room temperature at a pressure of 10-50 bar.

In an exemplary embodiment, the thermochemical conversion reaction may be performed at 200-300° C.

In another exemplary embodiment, the thermochemical conversion reaction may be performed at 200° C. or higher, 210° C. or higher, 220° C. or higher, 230° C. or higher, 240° C. or higher, 250° C. or higher, 260° C. or higher, 270° C. or higher, 280° C. or higher or 290° C. or higher, and 300° C. or lower, 290° C. or lower, 280° C. or lower, 270° C. or lower, 260° C. or lower, 250° C. or lower, 240° C. or lower, 230° C. or lower, 220° C. or lower or 210° C. or lower. For example, the thermochemical conversion reaction may be specifically performed at 200-275° C., 225-275° C., 225-250° C. or 250-275° C. in terms of the production yield of lactic acid.

In an exemplary embodiment, the thermochemical conversion reaction may be performed for 20-70 minutes.

In another exemplary embodiment, the thermochemical conversion reaction may be performed for 20 minutes or longer, 25 minutes or longer, 30 minutes or longer, 35 minutes or longer, 40 minutes or longer, 45 minutes or longer, 50 minutes or longer, 55 minutes or longer, 60 minutes or longer or 65 minutes or longer, and 70 minutes or shorter, 65 minutes or shorter, 60 minutes or shorter, 55 minutes or shorter, 50 minutes or shorter, 45 minutes or shorter, 40 minutes or shorter, 35 minutes or shorter, 30 minutes or shorter or 25 minutes or shorter. For example, the thermochemical conversion reaction may be performed for 25-65 minutes or 30-60 minutes in terms of the production yield of lactic acid.

In an exemplary embodiment, the thermochemical conversion reaction may be performed in a batch reactor.

In another aspect, the present disclosure provides a method for producing lactic acid from wastes, which includes: a step of adding waste paper including cellulose and/or hemicellulose, water and a lanthanide triflate catalyst into a reactor; a step of supplying an inert gas into the reactor; and a step of performing thermochemical conversion reaction by heating the reactor under inert atmosphere.

In another aspect, the present disclosure provides lactic acid produced by the method.

In another aspect, the present disclosure provides a catalyst for thermochemical conversion reaction of wastes containing cellulose and/or hemicellulose, which includes a lanthanide metal component and is used for producing lactic acid from wastes containing cellulose and/or hemicellulose.

In an exemplary embodiment, the lanthanide metal component may be lanthanide triflate.

In an exemplary embodiment, the lanthanide triflate may be one or more selected from a group consisting of lanthanum triflate, cerium triflate, praseodymium triflate, neodymium triflate, promethium triflate, samarium triflate, europium triflate, gadolinium triflate, terbium triflate, dysprosium triflate, holmium triflate, erbium triflate, thulium triflate, ytterbium triflate and lutetium triflate.

In an aspect, the catalyst allows production of lactic acid from wastes containing cellulose and/or hemicellulose with high yield and selectivity in short time. For example, the available sugars (glucose, xylose, etc.) contained in the raw material may be converted to lactic acid at an efficiency of about 60%.

Hereinafter, the present disclosure will be described more specifically through examples. The examples provided only for illustration of the present disclosure and it will be obvious to those having ordinary skill in the art that the scope of the present disclosure is not limited by the examples.

Example 1

A dried waste corrugated paperboard was cut to a size of 0.5 cm×0.5 cm. 200 mg of the prepared waste corrugated paperboard was added to a batch reactor after mixing well with 25 mL of water. Together with this, 0.05 mmol of one of lanthanum triflate (La(OTf)$_3$), neodymium triflate (Nd(OTf)$_3$), ytterbium triflate (Yb(OTf)$_3$), erbium triflate (Er(OTf)$_3$) catalysts was added and the reactor was filled with 30 bar of helium at room temperature. Then, after heating the reactor to 250° C., thermochemical conversion reaction was performed for 30 minutes while stirring at 300 rpm. After cooling the reactor again to room temperature, the yield of lactic acid was calculated from the liquid reaction product according to the following equation.

Yield of lactic acid (mol %)=(Produced lactic acid (mol))/((2×C$_6$ monosaccharides in raw material (mol))+(C$_5$ monosaccharides in raw material (mol))×100

FIG. 2 shows a result of quantifying the lactic acid produced through the thermochemical conversion reaction. It was confirmed that lactic acid was obtained with a yield of about 55-66 mol % based on the cellulose- and hemicellulose-derived monosaccharides in the waste corrugated paperboard.

Example 2

Thermochemical conversion reaction was performed in the same manner as in Example 1, except that erbium triflate (Er(OTf)$_3$) was used as a catalyst and the thermochemical conversion reaction temperature was varied from 200 to 275° C.

The result of analyzing the yield of lactic acid is shown in FIG. 3. As seen from FIG. 3, the yield of lactic acid was about 40 mol % or higher when the thermochemical conversion reaction was performed at 225-275° C. The highest lactic acid yield was achieved when the thermochemical conversion reaction was performed at 250° C.

Example 3

Thermochemical conversion reaction was performed in the same manner as in Example 1, except that erbium triflate (Er(OTf)$_3$) was used as a catalyst and the thermochemical conversion reaction time was varied from 30 minutes to 1 hour.

The result of analyzing the yield of lactic acid is shown in FIG. 4. As seen from FIG. 4, the highest lactic acid yield was achieved when the thermochemical conversion reaction was performed for 30 minutes.

Comparative Example 1

Thermochemical conversion reaction was performed in the same manner as in Example 1, except that zinc chloride (ZnCl$_2$), which is a commonly used Lewis acid catalyst, was used as a catalyst and the thermochemical conversion reaction temperature was performed at 250° C. for 30 minutes.

The result of analyzing the yield of lactic acid is shown in FIG. 5. As seen from FIG. 5, when thermochemical conversion reaction was performed using the zinc chloride Lewis acid catalyst instead of the lanthanide metal catalyst, lactic acid was produced at a yield of about 23 mol %.

Comparative Example 2

Thermochemical conversion reaction was performed in the same manner as in Example 1, except that aluminum chloride (AlCl$_2$), which is a commonly used Lewis acid catalyst, was used as a catalyst and the thermochemical conversion reaction temperature was performed at 250° C. for 30 minutes.

The result of analyzing the yield of lactic acid is shown in FIG. 5. As seen from FIG. 5, when thermochemical conversion reaction was performed using the aluminum chloride Lewis acid catalyst instead of the lanthanide metal catalyst, lactic acid was produced at a yield of about 5 mol %.

Comparative Example 3

Thermochemical conversion reaction was performed in the same manner as in Example 1, except that zinc triflate (Zn(OTf)$_2$) was used as a catalyst and the thermochemical conversion reaction was performed at 250° C. for 30 minutes.

The result of analyzing the yield of lactic acid is shown in FIG. 5. As seen from FIG. 5, when thermochemical conversion reaction was performed using the zinc triflate catalyst containing zinc metal instead of the lanthanide metal catalyst, lactic acid was produced at a yield of about 39 mol %.

As described above, it was confirmed that the yield of lactic acid was significantly lower when the Lewis acid catalyst or the zinc triflate catalyst was used in Comparative Example 1-3 as compared to when the lanthanide metal catalyst was used under the same condition. Accordingly, it was confirmed that the yield of lactic acid can be increased effectively by using the lanthanide metal catalyst when producing lactic acid from wastes through thermochemical conversion reaction.

While specific exemplary embodiments of the present disclosure have been described in detail above, it will be obvious to those having ordinary knowledge in the art that the foregoing description is given only as specific exemplary embodiments and the scope of the present disclosure is not limited thereby. It is to be noted that the substantial scope of the present disclosure is defined by the appended claims and their equivalents.

The invention claimed is:

1. A method for producing lactic acid from wastes, comprising adding a metal catalyst to wastes containing cellulose and/or hemicellulose,
wherein the metal catalyst is erbium triflate or ytterbium triflate, and the wastes are waste paper.

2. The method for producing lactic acid from wastes according to claim 1, wherein the metal catalyst is added in an amount of 0.25-0.5 mmol per 1 g of the wastes.

3. The method for producing lactic acid from wastes according to claim 1, wherein the metal catalyst is added after the wastes are mixed with a solvent.

4. The method for producing lactic acid from wastes according to claim 1, wherein the method further comprises performing thermochemical conversion reaction after adding the metal catalyst.

5. The method for producing lactic acid from wastes according to claim 4, wherein the thermochemical conversion reaction is performed at 200-300° C.

6. The method for producing lactic acid from wastes according to claim 4, wherein the thermochemical conversion reaction is performed for 20-70 minutes.

* * * * *